United States Patent [19]
Vonk et al.

[11] Patent Number: 5,741,312
[45] Date of Patent: Apr. 21, 1998

[54] PACEMAKER SYSTEM AND METHOD WITH IMPROVED CAPTURE DETECTION AND THRESHOLD SEARCH

[75] Inventors: Bernardus F. M. Vonk, Wehl; Geeske van Oort, Nieuwleusen; Johannes S. van der Veen, Dieren, all of Netherlands

[73] Assignee: Vitatron Medical, B.V., Dieren, Netherlands

[21] Appl. No.: 820,445

[22] Filed: Mar. 12, 1997

[51] Int. Cl.$^6$ ................................... A61N 1/362
[52] U.S. Cl. ............................. 607/28; 607/11
[58] Field of Search .................... 607/11, 13, 27, 607/28

[56] References Cited

U.S. PATENT DOCUMENTS

| | | | |
|---|---|---|---|
| 3,835,865 | 9/1974 | Bowers | 128/419 P |
| 4,305,396 | 12/1981 | Wittkampf et al. | 128/419 PG |
| 4,343,312 | 8/1982 | Cals et al. | 128/419 PG |
| 4,674,508 | 6/1987 | DeCote | 607/28 |
| 5,320,643 | 6/1994 | Roline et al. | 607/28 |
| 5,476,487 | 12/1995 | Sholder | 607/28 |

*Primary Examiner*—William E. Kamm
*Assistant Examiner*—Kennedy J. Schaetzle
*Attorney, Agent, or Firm*—Woodcock Washburn Kurtz Mackiewicz & Norris LLP

[57] ABSTRACT

There is provided a pacemaker system with capture verification and threshold testing, in which the pacemaker waits after each change in delivered pace pulses for a stabilization interval, in order to minimize polarization and enhance capture verification. The threshold test utilizes a pace pulse pair, comprising a prior search pulse which is varied during the test, and the regular pacing pulse which is above threshold. When delivery of the pulse pairs is initiated, the search pulse is adjusted to optimize polarization, and the pacemaker waits for predetermined stabilization period of time in order to allow for minimum polarization and to optimize capture detection. The search pulse is increased incrementally in output value toward threshold, and following each such increase the pacemaker waits for a stabilization interval. The pacemaker detects when capture is achieved by the search pulse, thereby providing an indication of threshold.

20 Claims, 4 Drawing Sheets

PACEMAKER SYSTEM AND METHOD WITH IMPROVED CAPTURE DETECTION AND THRESHOLD SEARCH

FIELD OF THE INVENTION

This invention relates to pacemaker systems and methods and, more particularly, pacemaker systems which provide for capture detection and automatic threshold determination.

BACKGROUND OF THE INVENTION

A chronic problem in the pacemaker art is that of minimizing the output energy of delivered stimulus pulses, either the ventricular pulse (VP) for a single chamber ventricular pacemaker, the atrial pulse (AP) for an atrial pacemaker, or both VP and AP for dual chamber pacemakers. Although battery sources have improved greatly in recent years, so too have capabilities for performing additional functions, such as obtaining and storing diagnostic data, telemetering such stored information or other pacemaker parameter data to an external programmer, etc. These new functions are enabled by dramatic advances in the area of data processing, particularly with the increased use of microprocessors and associated memory. Accordingly, whatever the battery capacity, the pacemaker manufacturer is constantly seeking additional ways to save energy so as to enable performance of additional functions while maintaining effective pacemaker lifetime. Thus, in designing future products it is more and more important to minimize the pulse output energy. This leads to the need for accurate measuring of evoked P and/or R waves, to determine whether or not a pace pulse has been effective in stimulating the heart. The technique of determining how low the output energy can be set is known as threshold searching, by which the threshold amount of energy needed to evoke cardiac response is determined. As is known in the art, once the threshold is determined, the pacing level can be set at some safe incremental level above threshold, to optimize the amount of energy delivered through the pace pulses.

The pacemaker patent literature reveals many different schemes for determining threshold to cardiac pacing. See, for example, U.S. Pat. Nos. 3,835,865; 4,305,396; 5,320,643; and 5,476,487. Most threshold searching arrangements rely on accurate sensing of the evoked response, i.e., determining whether the delivered pace pulse "captures" or evokes a cardiac response. Minimization of the electrode polarization at the electrode where the pulse is delivered, and which follows a delivered pace pulse, is essential in measuring the evoked potential, or evoked response. If a large degree of polarization exists, it is difficult to detect an evoked response at the electrode. See U.S. Pat. No. 4,343,312, which provides an output circuit for delivering a triphasic pace pulse designed to minimize polarization and better enable detection of capture or no capture.

The present invention is based on the observation that reliable threshold search implementation requires a stable polarization environment. Thus, reliable capture detection can take place only when polarization has been minimized and stabilized, which condition should be achieved to the fullest possible extent before proceeding with the threshold testing. It is accordingly an object of this invention to provide a system and method for capture detection and threshold determination which includes minimization and stabilization of polarization.

SUMMARY OF THE INVENTION

There is provided a pacemaker system and method which incorporates the capability of detecting capture by a delivered pace pulse; and threshold to a delivered pace pulse, either VP or AP, the threshold determination being carried out after optimizing polarization caused by delivery of pace pulses. Upon initiating a threshold search, the pacemaker utilizes pairs of separate stimulus pulses, spaced 50–100 ms from each other. The ongoing regular pace pulses, presumed to be above threshold, are adjusted for minimal polarization and optimal P, R or T-wave sensing. A second, or search pulse is generated 50–100 ms before the regular pulse, initially at a relatively small output which is below threshold. The search pulse is adjusted for minimal polarization, preferably using the adjustment criteria adopted for the regular pace pulses. In order to provide stabilization, the pulse pairs are delivered at constant output levels for a predetermined stabilization period, e.g., 1–20 stabilization pulses. After this, capture is determined by looking for an evoked response first following the relatively low level search pulse, and then following the higher level regular pulse; optionally the time from delivery of the second pulse to detection of the T-wave can also be used to verify whether the search pulse or the regular pace pulse evoked capture. If capture is not found, the search pulse is adjusted to a new and higher value, and again the test waits for a number of stabilization pulses before looking for an evoked response. The steps of increasing the search pulse toward threshold and waiting a predetermined stabilization period, and only then looking for capture, is repeated until it is found that the search pulse has captured the heart, thereby indicating threshold. After this, the regular pace pulse is adjusted as a function of the determined threshold.

DESCRIPTION OF THE PREFERRED EMBODIMENTS

Figure 1:
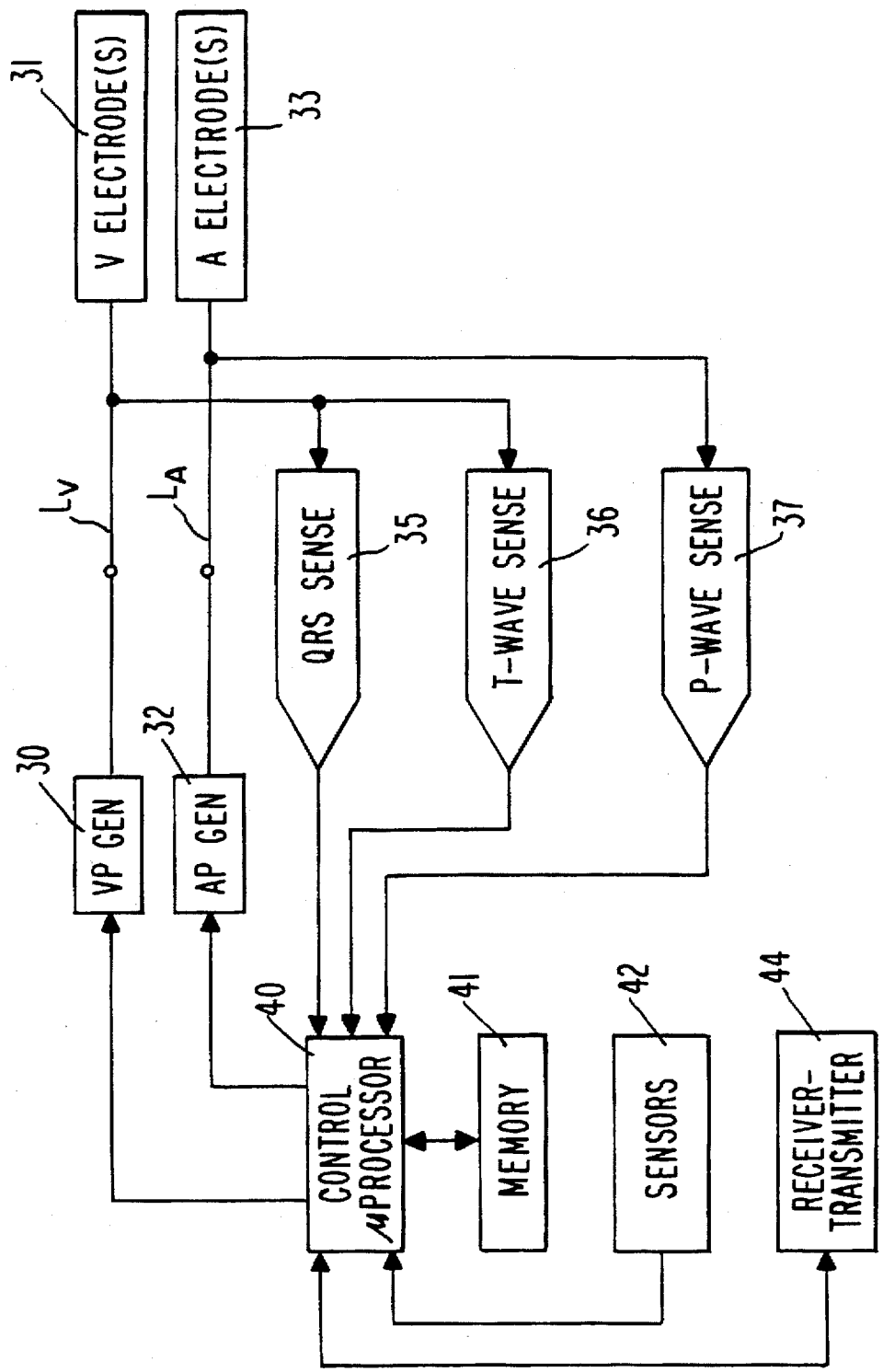
FIG. 1 is a block diagram showing the primary elements of a pacemaker system in accordance with this invention, having incorporated in it a routine for capture detection and threshold search.

Referring now to FIG. 1, there is shown a block diagram of an illustrative pacemaker system for use in the practice of this invention. The block diagram of FIG. 1 shows the primary functional components of a pacemaker, which components and their interconnections are well known in the pacemaker art. A VP generator 30 produces ventricular pace pulses, including pulse pairs as used in his invention, under control of control block 40. The output of generator 30 is connected through a pacing lead $L_v$, to a ventricular electrode or electrodes indicated at 31, for pacing of the patient's ventricle. The electrode or electrodes 31 also sense signals in the patient's ventricle, natural and evoked. Signals sensed at electrodes 31 are connected to a QRS sense amplifier circuit 35, as well as to a T-wave sense amplifier 36. By a technique well known in the art, amplifier 35 is enabled for a window corresponding to the expected arrival of the QRS, under control of circuit 40; similarly the T-wave amplifier is enabled for a window of time around the expected T-wave, likewise under the control of circuit 40. Thus, ventricular senses (VS) and T-waves are detected and inputted into control 40, for use by the pacemaker. For a dual chamber pacemaker, there is also an atrial pulse generator 32, which delivers atrial pace pulses under control of control circuit 40. These pulses are connected through an atrial lead $L_A$ to atrial electrode or electrodes designated at 33. Natural P-waves, or evoked atrial responses, are sensed by the atrial electrodes 33, and connected to P-wave sense amplifier 37, the output of which is connected back to control block 40. Sense amplifier 37 may also switchably be enabled for a window of time corresponding to the expected arrival of the P-wave.

Control block 40 performs the various logic and processing functions of a modern pacemaker, and suitably comprises a microprocessor. The microprocessor circuit itself contains some memory, and there may be additional memory, RAM/ROM, as indicated at block 41. The allocation of hardware and software to the structure and control block 40 is a matter of design choice, and not important to the scope of this invention. Also shown are sensors 42, for determining one or more parameters from which rate responsive control can be achieved, again in a known fashion. Block 44 illustrates a receiver-transmitter for communicating with an external programmer by telemetry, in a known fashion. Thus, program instructions from an external transmitter are received at 44 and coupled into control block 40; likewise data collected by the pacemaker concerning pacemaker operating variables and/or diagnostic data may be downloaded through unit 44 to the external programmer, in a known manner.

Figure 2A:
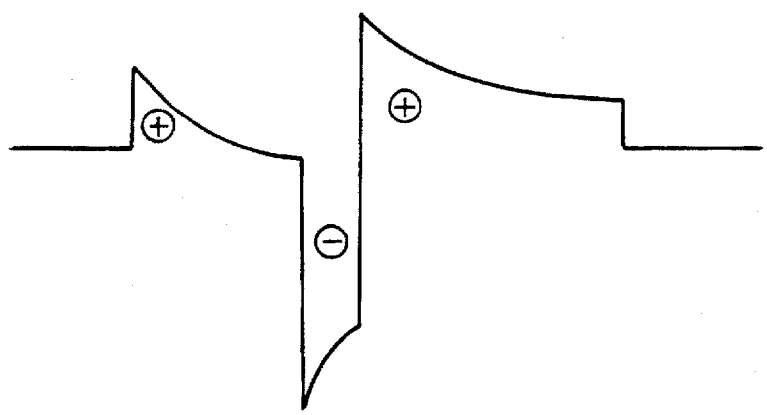
FIG. 2A is a diagram of a triphasic pace pulse designed to minimize polarization.

Referring now to FIG. 2A, there is shown a representative triphasic pace pulse designed to minimize polarization produced by delivery of a pace pulse through an implanted electrode. The triphasic pulse comprises a first positive going portion, a larger negative going portion which is designed to evoke the cardiac response, and a follow-up positive going portion. The parameters, i.e., magnitude and duration, of the respective portions of the triphasic pulse are adjusted to determine the combination which optimally minimizes polarization. As an example of such an adjustment, see U.S. Pat. No. 4,343,312, incorporated herein by reference. In a currently preferred embodiment, only fixed resistors are used for setting the pre- and post-change periods. The optimum adjustment can be obtained by delivering pulses which have outputs either below or above threshold. The height and width of the respective pulse portions are programmed to different values, with observation of the resulting polarization, and comparison of the produced polarization for different combinations of the positive and negative portions. Alternately, adjusting for minimum polarization can be carried out automatically by the pacemaker. When minimization of the polarization is found, data relating to the polarization signal, or a "polarization template" can be stored and used for comparison when subsequent changes in the stimulus pulse are evaluated. Note that as used herein, the terms minimize and minimization refer to reducing polarization, it being understood that absolute minimization is not obtainable.

Figure 2B:
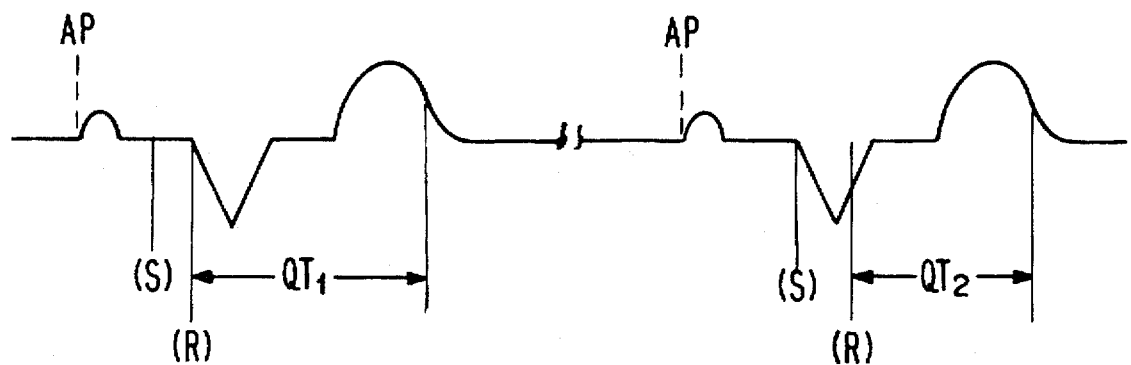
FIG. 2B is a timing diagram indicating delivery of pulse pairs to a patient's ventricle, each pair comprising a first search pulse and a second regular pace pulse, illustrating how ventricular capture by the search pulse can be detected.
Figure 2C:
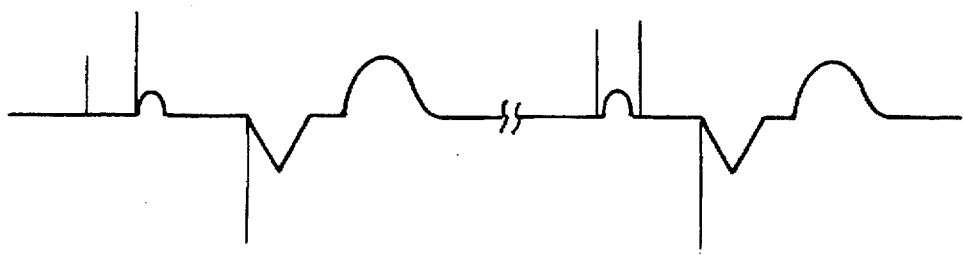
FIG. 2C is a timing showing capture detection by delivery of similar pulse pairs to a patient's atrium.

Referring to FIG. 2B, there is shown a timing diagram illustrating delivery of a pair of pulses in accordance with this invention, e.g., a first search pulse and a second regular pacing pulse. FIG. 2B shows a threshold test being performed for ventricular pacing. Following a first atrial pulse and resulting atrial evoked response and an AV delay, a search pulse (S) and regular pulse (R) are delivered. As indicated, the regular pulse captures the ventricle, resulting in a QRS complex and T-wave. The time between the delivery of the regular pace pulse and the T-wave is indicated as $Q-T_1$. At a later time, after the search pulse output level has been raised above threshold and stabilized, it is seen that the search pulse captures the ventricle, not the regular pulse, and that $QT_2$ is decreased relative to $QT_1$. FIG. 2C is a similar timing diagram, applied to the threshold test for atrial pace pulses, again showing a first pair where the search pulse does not capture the atrium, and second pair where the search pulse does capture the atrium. It is to be noted that FIGS. 2B and 2C are illustrative of the timing involved, and that the intracardiac signals as seen by an implanted pacemaker may differ slightly in ways that are not relevant to the explanation of this invention.

Figure 3A:
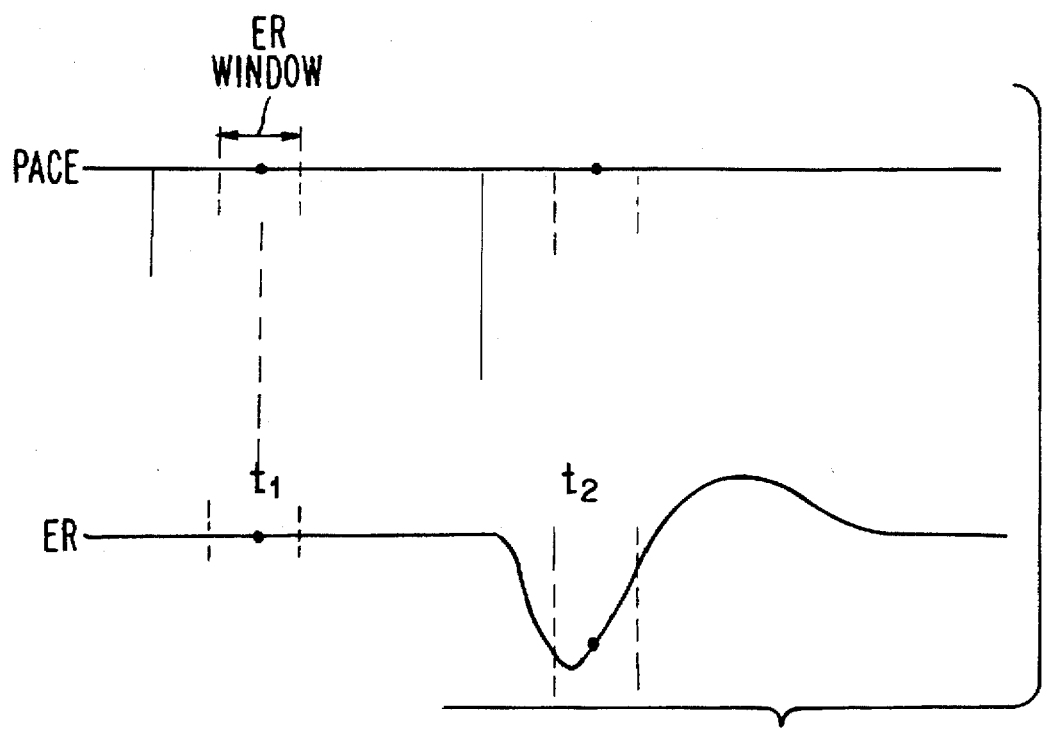
FIG. 3A comprises a pair of timing diagrams which illustrate the use of a sensing window, where the regular pulse captures the heart.
Figure 3B:
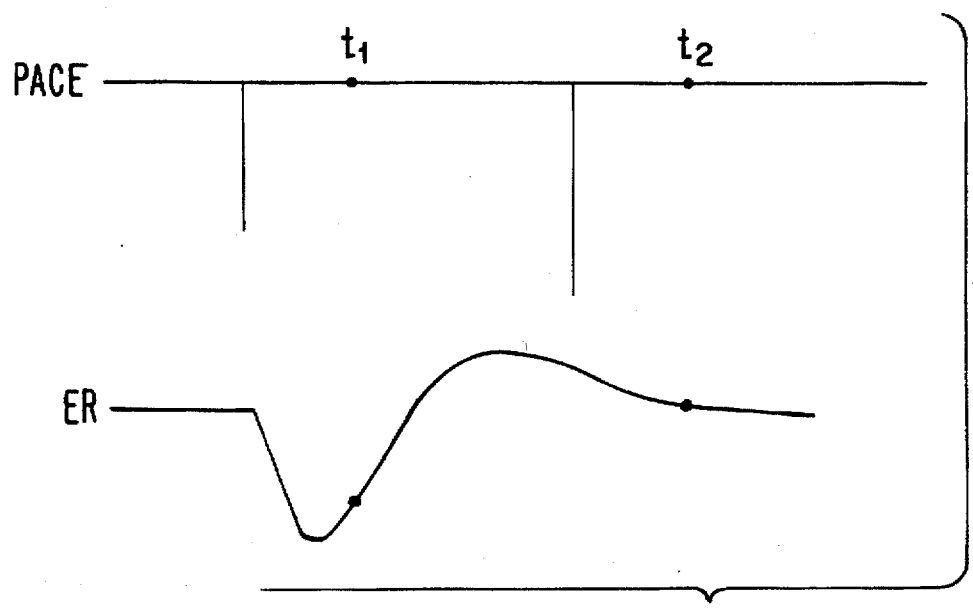
FIG. 3B is a similar pair of timing diagrams illustrating use of a sensing window, where the search pulse of the pulse pair captures the heart.

Referring to FIG. 3A, there is illustrated the technique of providing an evoked response window following each delivered pace pulse, for determining whether there has been an evoked response. As seen in the upper timing diagram of FIG. 3A, a first search pulse is delivered, and an evoked response window is timed out centered about a time $t_1$ following the search pulse. As seen in the lower timing diagram, the search pulse does not evoke a response, and there is no detected evoked response during the search window. When the regular pace pulse is delivered, a window is timed out centered about time $t_2$ following the regular pulse, and during this regular window the sense amplifier sees the evoked response. Referring to FIG. 3B, the same pulse pair is shown, but in this instance the evoked response is seen during the search window centered around time $t_1$. This window technique enhances specific detection of the evoked response, i.e., for determining whether it was the search pulse or the regular pulse that evoked the response.

Figure 4:
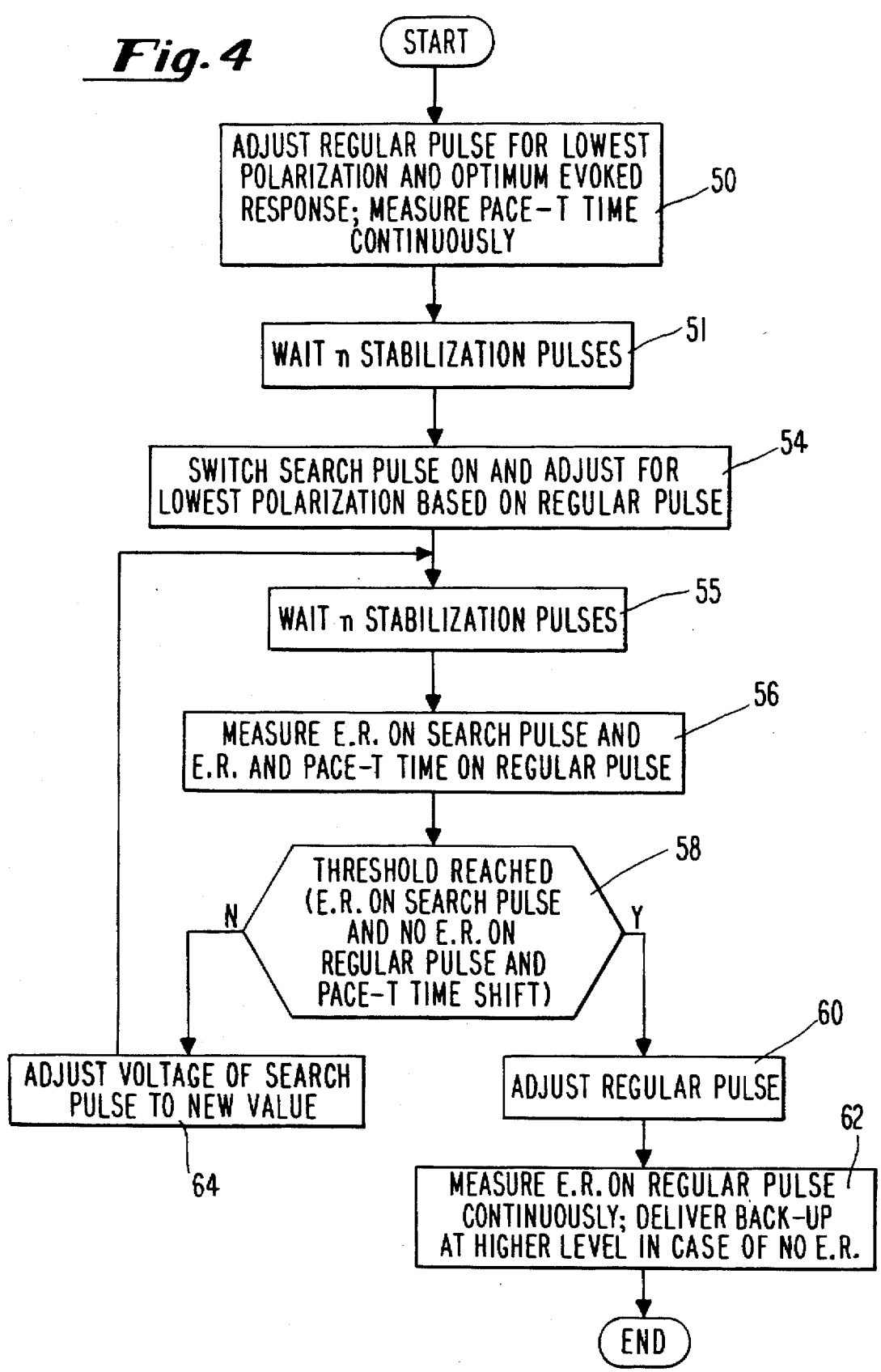
FIG. 4 is a flow diagram showing the primary steps of a threshold detection routine in accordance with this invention.

Referring now to FIG. 4, there is shown a flow diagram of the primary steps in carrying out the capture detection and threshold search feature of this invention. The algorithm starts by adjustment of the regular pulse for lowest polarization and optimum evoked response, as indicated at 50. Such adjustment may be made as discussed above, i.e., adjusting one or more parameters of the pulse. Following this, the pacemaker measures the pace-T time, or "QT" interval, continuously. As indicated at 51, the test waits for a predetermined number n of delivered pulses, to allow stabilization of the polarization pattern. The stabilization can vary, and the waiting period is a matter of design choice. For example, n can vary between 0 and 20. However, it is an important feature to make sure that there is stabilization period. Following this, as indicated at 54, the pacemaker begins to deliver pulse pairs, switching on a second, search pulse, and adjusting the search pulse for lowest polarization. Here, the adjustment of the search pulse may be made based on the adjustment of the triphasic pulse components made for the regular pulse, i.e., the same relative heights and widths of the pulse portions may be utilized. Following this, as indicated at 55, the pacemaker again waits a predetermined time, e.g., 10 stabilization pulses. Only after both the regular pulse and the search pulse have been stabilized, is measurement of the evoked response undertaken. Optionally, at the end of the stabilization interval, the polarization pattern for the search pulse can be compared with a previously stored template; if the difference is too great, either the search pulse is further adjusted or the stabilization interval is extended until polarization is satisfied.

At 56, evoked response is sensed following the search pulse and the regular pulse, and the pace-T time relative to the regular pulse is measured. Following this, at 58, it is determined whether the threshold has been reached, i.e., whether an evoked response is sensed by the sense amplifier following the search pulse. Optionally, as indicated, threshold can be verified by examining the pace-T time interval, and determining whether it has shifted, as discussed above. Of course, at the beginning of the test, it is anticipated that the search pulse output level has been set below threshold, such that it does not capture. Accordingly, the routine exits to block 64, and adjusts the search pulse output upwardly to a new value. The routine then goes back to block 55, and again waits for 10 stabilization pulses before going to the steps of capture detection and threshold determination. Thus, the routine may cycle a number of times until the search pulse has incremented above threshold. Importantly, each time the search pulse output is incremented, a new stabilization interval is invoked, in order to minimize polarization and enable reliable capture detection.

It is to be understood that block 58 can be modified. For example, the pacemaker can look for 1, 2, 3 . . . or n delivered pulse pairs where the search pulse is determined to capture the heart, where n can be 2 or greater to ensure that threshold has been reached.

After threshold has been reached by the search pulse, the routine branches to step 60 and, if desired, adjusts the regular pulse accordingly, i.e., at a safety value above threshold. Following this, as indicated at 62, the pacemaker paces continuously with the regular pulse, measuring evoked response on each delivered pulse. In the case of no evoked response, a back-up pulse can be delivered to avoid skipping a heartbeat. Note that adjustment at step 60 may not be required, particularly if the change would be very little. Also, the pacemaker may be programmed to periodically obtain a threshold reading only for diagnostic purposes, e.g., to record threshold trend, construct a threshold histogram, etc.

It is to be understood that the capture detection and search features of this invention can be employed during clinical follow-up, in which case it is initiated by an external programmer. In this setting, the measured values will be communicated to the programmer, and the physician can re-program pace pulse output level as indicated. Alternately, the feature can be performed automatically, e.g., after a programmable period such as 12 or 24 hours. The threshold value that has been found is stored by the pacemaker, and upon next initiating a threshold test, the search pulse is set at a predetermined level relative to the last determined threshold, to optimize the test procedure. For example, if the latest measured threshold value was 0.5V, the rest can start automatically with a search pulse at 0.4V and a regular pulse at the regular output (for example 2.5V). If 0.4V does not result in capture, the next search pulse amplitude will be 0.6V (right above the previous threshold value). This way, the threshold procedure will be performed in a minimal amount of time.

In the practice of this invention, the capture detection feature can be used without a threshold detection test. Thus, the pacemaker may be enabled to automatically adjust the stimulus pulse parameters, wait out a stabilization period, and proceed with capture detection. In the event that an evoked response is not sensed at any time, a back-up stimulus is delivered, and the stimulus output is adjusted upward by a predetermined increment.

We claim:

1. A pacemaker system for pacing a patient, having stimulus means for generating and delivering stimulus pulses to said patient, ER means for sensing when a delivered stimulus pulse has evoked a response, and threshold means for determining a measure of pacing threshold to delivered stimulus pulses, said threshold means comprising:

pulse pair means for controlling said stimulus means to cyclically generate and deliver pairs of stimulus pulses, the first pulse of each said pair being variable in output and the second pulse of said pulse pairs being a regular pacing pulse at an output level above the pacing threshold;

stabilization means for determining when said pulse pairs have been delivered for at least a predetermined stabilization period;

detection means operable at the end of said stabilization period for detecting which pulse of a said pulse pair delivered after said stabilization period evoked a heart response;

repeat means operable following a detection that said regular pulse evoked a cardiac response, for incrementing said first pulse output and for enabling said stabilization means to determine when stimulus pulse pairs with an incremental first pulse output have been delivered for a stabilization period following said incrementing;

threshold measuring means for determining when said incremented first pulse results in an evoked response, and for then storing the first pulse output value as said measure of pacing threshold; and setting the output value of said stimulus pulses as a function of said measure of threshold.

2. The system as described in claim 1, wherein said threshold means further comprises first adjusting means for adjusting at least one predetermined parameter of said first pulse to minimize polarization prior to said stabilization.

3. The system as described in claim 2, wherein said pulse pair means comprises means for generating said first pulse at a time within the range of about 50–100 ms before said second pulse.

4. The system as described in claim 2, wherein both of said first and second pulses have controllable positive and negative portions having adjustable magnitude and duration parameters.

5. The system as described in claim 4, comprising second adjusting means for adjusting at least one output parameter of said second pulse to minimize polarization.

6. The system as described in claim 5, wherein said first adjusting means comprises means for setting said at least one first pulse parameter to correspond to the corresponding parameter of said second pulse.

7. The system as described in claim 1, comprising polarization means for detecting polarization due to a delivered pulse and comparing said detected polarization to a predetermined polarization pattern.

8. The system as described in claim 1, wherein said pulse pair means comprises means for controlling said stimulus means to generate said first and second pulses as triphasic pulses, and control means for controlling the shape of said triphasic pulses so as to minimize polarization.

9. The system as described in claim 1, wherein said stimulus means has means for delivering stimulus pulses to the patient's ventricle.

10. The system as described in claim 1, wherein said stimulus means has means for delivering stimulus pulses to the patient's atrium.

11. A method used in an implanted cardiac pacemaker for detecting when a stimulus pulse delivered to an electrode positioned in the patient's heart evokes a cardiac response, comprising:

adjusting said stimulus pulse to minimize resulting polarization sensed at said electrode following the delivered pulse;

pacing with adjusted stimulus pulses for a predetermined stabilization interval;

upon conclusion of the stabilization interval, delivering a next adjusted stimulus pulse, sensing the signal at said electrode; and determining from said sensed signal whether it represents an evoked cardiac response.

12. The method as described in claim 11, comprising delivering at least n adjusted stimulus pulses during said stabilization interval, where n is a predetermined number having a maximum value of about 20.

13. The method as described in claim 11, wherein said step of delivering an adjusted stimulus pulse comprises generating a stimulus pulse with at least a first portion of a positive polarity and a second portion of a negative polarity, and said adjusting comprises adjusting at least one of said portions.

14. The method as described in claim 13, comprising generating a triphasic stimulus pulse.

15. The method as described in claim 11, wherein said determining step comprises determining whether a T-wave is evoked within a predetermined interval following delivery of said next adjusted stimulus pulse.

16. The method as described in claim 15, comprising determining when said next adjusted stimulus pulse does not evoke a response, further adjusting said stimulus pulse, pacing with said further adjusted stimulus pulses and thereafter determining whether a said further adjusted stimulus pulse evokes a cardiac response.

17. A cardiac pacemaker system, having a stimulus generator for generating stimulus pulses, lead delivery means for delivering said pulses to at least one electrode positioned in a patient's heart, sensing means for sensing electric signals at said electrode following delivery of a stimulus pulse, and capture means for determining when a delivered stimulus has evoked a cardiac response, said capture means comprising:

polarization control means for adjusting at least one parameter of said stimulus pulses so as to minimize polarization at said electrode resulting from a delivered pace pulse, stabilization control means for determining when said stimulus generator has generated said adjusted stimulus parameters for at least a predetermined stabilization interval, and detection means operative after said stabilization interval for sensing the signals at said electrode following one or more delivered adjusted stimulus pulses, and for determining from said sensed signal or signals whether said stimulus pulse is capturing the patient's heart.

18. The system as described in claim 17, wherein said stabilization control means comprises interval means for maintaining said stabilization interval for n adjusted stimulus pulses.

19. The system as described in claim 18, wherein said interval means comprises means for setting n to a number between 1 and 20.

20. The system as described in claim 17, comprising pulse pair means for controlling said stimulus generator to generator stimulus pulse pairs, and wherein said polarization control means comprises means for adjusting at least one parameter of each stimulus of said pulse pairs.

* * * * *